United States Patent [19]

Brüning et al.

[11] Patent Number: 5,166,342
[45] Date of Patent: Nov. 24, 1992

[54] DIMETHYLFURYL-DIHYDRO-1,3,5-DITHIAZINES

[75] Inventors: Jürgen Brüning; Roland Emberger; Matthias Güntert; Rudolf Hopp; Manfred Köpsel, all of Holzminden; Peter Werkhoff, Hoexter, all of Fed. Rep. of Germany

[73] Assignee: Haarmann & Reimer, Holzminden, Fed. Rep. of Germany

[21] Appl. No.: 777,817

[22] Filed: Oct. 15, 1991

[30] Foreign Application Priority Data

Oct. 24, 1990 [DE] Fed. Rep. of Germany ....... 4033809

[51] Int. Cl.$^5$ ........................................... C07D 285/15
[52] U.S. Cl. ........................................................ 544/5
[58] Field of Search ............................................ 544/5

[56] References Cited

U.S. PATENT DOCUMENTS

| 2,727,036 | 12/1955 | McDermott | 544/5 |
| 3,966,988 | 6/1976 | Wilson et al. | 544/5 |
| 4,200,741 | 4/1980 | Chu et al. | 544/5 |
| 4,647,662 | 3/1987 | Bruning et al. | 544/5 |

FOREIGN PATENT DOCUMENTS 0186026  7/1986  European Pat. Off. .

Primary Examiner—John M. Ford
Attorney, Agent, or Firm—Sprung Horn Kramer & Woods

[57] ABSTRACT

Dimethylfuryl-dihydro-1,3,5-dithiazines are useful flavorings having low taste threshold values. They impart a coffee or mocha taste, in particular to drinks, confectionery and bakery products.

1 Claim, No Drawings

DIMETHYLFURYL-DIHYDRO-1,3,5-DITHIAZINES

The invention relates to new dimethylfuryl-dihydro-1,3,5-dithiazines, to a process for their preparation by cyclocondensation of 2-furfural, acetaldehyde, ammonia and hydrogen sulphide (or ammonium sulphide) and to the use of these new compounds as flavourings.

The new compounds correspond to the formula

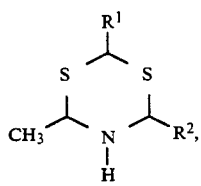

in which $R^1$ and $R^2$ are different and represent methyl or 2-furyl (so that therefore one substituent denotes methyl and the other 2-furyl).

The terms "furfural" and "furyl" below in each case denote "2-furfural" and "2-furyl".

The compounds (I) according to the invention can be obtained by reaction of furfural, acetaldehyde, ammonia and hydrogen sulphide; ammonia and hydrogen sulphide can be replaced by ammonium sulphide. Since the corresponding methyldifuryl derivative and the corresponding 2,4,6trimethyl derivative, but also the analogous tetrahydrothiadiazines can also be formed as undesired by-products, it has been attempted to drive the reaction in the desired direction by choice of the molar ratios of the starting components. The molar ratio acetaldehyde/furfural is in general 1.5 to 5, preferably 2 to 4, in particular 2.5 to 3.5. Ammonia is as a rule employed in a small excess, preferably in amounts of >1.0 to 1.4, in particular 1.05 to 1.15, mol per mol of furfural, it being possible to introduce ammonia as a gas, or, preferably, to employ it in the form of an aqueous solution (in general 10 to 33, preferably 20 to 30% strength by weight).

Hydrogen sulphide is employed in an amount corresponding approximately to the stoichiometrically calculated ratio, the saturation of the reaction mixture being indicated during the introduction by escape of hydrogen sulphide. The reaction can be carried out in substance, in water or in polar (preferably water-miscible) inert organic solvents, water being preferred. At its simplest, the reaction is carried out in water. The concentration of the components in the solvent is not critical; however, it is attempted to keep the solvent volume within limits for practical reasons: 10 to 1,000, preferably 50 to 200, ml of solvent per mol of furfural can in general be considered a suitable amount.

Owing to the boiling point of acetaldehyde of 20.2° C., provided it is not desired to work under pressure, a temperature between 0 and 20, in particular from 5° to 10° C., is chosen for the reaction.

The compounds (I) according to the invention can be isolated by extraction with an organic solvent, for example toluene, from the aqueous reaction solution, removal of the organic solvent and purification by means of a suitable method, for example chromatography, preferably high pressure liquid chromatography (HPLC). Since the two isomers (I) are formed together, it has to be decided whether it is desired to employ the crude isomer mixture as such for the planned application or—with a somewhat higher expenditure on isolation—to isolate the pure isomers. (If the reaction is not carried out in an aqueous medium, the method has to be modified in a suitable manner).

The invention thus relates to dimethylfuryl-dihydro-1,3,5-dithiazines of the formula (I).

The invention further relates to a process for the preparation of these compounds (I) by reaction of furfural, acetaldehyde, ammonia and hydrogen sulphide, if appropriate in the presence of a solvent.

The compounds (I) according to the invention are useful flavourings which are distinguished by low taste threshold values. (All data below in percentages, in ppm or in ppt relate to the weight).

The taste threshold value for 4,6-dimethyl-2-furyl-dihydro-1,3,5-dithiazine, tested by 5 specially trained testers, in 5% strength aqueous sugar solution is thus <5 ppt, the taste threshold value for 2,6-dimethyl-4-furyl-dihydro-1,3,5-dithiazine under the same conditions is <100 ppt.

The taste description, determined in 5% strength aqueous sugar solution, for 4,6-dimethyl-2-furyl-dihydro-1,3,5-dithiazine (at a dosage of 150 ppt) is: mocha, burnt, coffee, bitter chocolate, cake crust, strongly roasted coffee.

The taste description, determined as described above for 2,6-dimethyl-4-furyl-dihydro-1,3,5-dithiazine (at a dosage of 1 ppm) is: coffee, mocha, roast character.

The flavouring compositions prepared using the compounds (I) according to the invention can be used in the entire foodstuffs and luxury goods field. They are in particular suitable for drinks, confectionery and bakery products. The compounds (I) according to the invention can be used in amounts from 100 ppt to 100 ppm, preferably 150 ppt to 1 ppm, relative to the ready-to-consume foodstuff. The compounds (I) according to the invention here can be employed in pure form, but also, for the sake of simplicity, in isomer mixtures, such as those obtained in the preparation.

The invention thus further relates to the use of the compounds (I) as flavourings.

In the examples below, percentage data in each case relate to the weight; parts are parts by weight.

EXAMPLES

Preparation 100 ml of water were initially introduced, and, with cooling, a mixture of 96 g (1 mol) of furfural and 132 g (3 mol) of acetaldehyde was metered in at a temperature of 5° to 10° C. 75 g (1.1 mol) of aqueous ammonia (25% strength) were then added at the same temperature and hydrogen sulphide was introduced until the mixture was saturated (about 7 hours). The mixture was left to stand overnight, whereupon it solidified to give a crystal magma. The organic components were dissolved by addition of 200 ml of toluene, and the organic phase was separated from the aqueous phase. After removing the solvent and the easily volatile components—in particular 99 g (0.6 mol) of 2,4,6-trimethyl-dihydro-1,3,5-dithiazine—by distillation, a solid residue of 34 g remained from which a mixture of 4,6-dimethyl-2-furyl-dihydro-1,3,5-dithiazine and 2,6-dimethyl-4-furyl-dihydro-1,3,5-dithiazine was separated by high pressure liquid chromatography (HPLC). A further HPLC separation gave the pure compounds in a ratio of the 2-furyl to 4-furyl isomers of 95:5.

For the HPLC separations, silica gel (100 Å, 10 μm) was used as the stationary phase, and pentane as the mobile phase. The column length was 25 cm and the column diameter 2 cm.

The isomers obtained were characterised by NMR spectroscopy (400 MHz, CDCl$_3$, tetramethylsilane as a standard):

| 2-furyl isomer | 4-furyl isomer |
|---|---|
| δ =7.379 ppm (1H,dd) | δ =7.388 ppm (1H,dd) |
| =6.35 ppm (2H,m) | =6.35 ppm (2H,m) |
| =5.552 ppm (1H,s) | =5.304 ppm (1H,d) |
| =4.272 ppm (2H,dq) | =4.390 ppm (1H,q) |
| =1.519 ppm (6H,d) | =4.234 ppm (1H,dq) |
| =0.9 ppm (1H,m) | =1.560 ppm (3H,d) |
|  | =1.535 ppm (3H,d) |
|  | =1.2 ppm (1H,t) |

Application 1

6 ppb of the mixture of 4,6-dimethyl-2-furyl- and 2,6-dimethyl-4-furyl-dihydro-1,3,5-dithiazine obtained by the above procedure were added to an instant coffee (made-up drink). In comparison to an unflavoured control sample, the flavoured sample had a distinctly more typical and more roasted coffee flavour.

Application 2

10 ppb of the mixture employed in Application 1 were added to a coffee substitute (made-up drink). In comparison to a control sample, the flavoured sample had a substantially more typical and more pleasant coffee flavour.

We claim:

1. Dimethylfuryl-dihydro-1,3,5-dithiazines of the formula

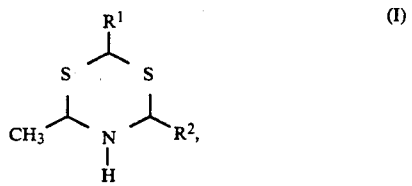

in which
R$^1$ and R$^2$ are different and represent methyl or 2-furyl.

* * * * *